(12) United States Patent
Heanue et al.

(10) Patent No.: US 8,755,866 B2
(45) Date of Patent: Jun. 17, 2014

(54) METHOD AND APPARATUS FOR LYMPH NODE MAPPING

(75) Inventors: John F. Heanue, San Jose, CA (US);
Joseph A. Heanue, Palo Alto, CA (US);
Brian P. Wilfley, Los Altos, CA (US);
Augustus P. Lowell, Durham, NH (US)

(73) Assignee: Covidien LP, Mansfield, MA (US)

( * ) Notice: Subject to any disclaimer, the term of this patent is extended or adjusted under 35 U.S.C. 154(b) by 642 days.

(21) Appl. No.: 11/381,443

(22) Filed: May 3, 2006

(65) Prior Publication Data

US 2007/0276257 A1 Nov. 29, 2007

(51) Int. Cl.
*A61B 6/00* (2006.01)

(52) U.S. Cl.
USPC ............. 600/476; 600/473; 359/10; 359/237; 359/238; 356/317

(58) Field of Classification Search
CPC ...... A61B 5/0059; A61B 5/415; A61B 5/418; G01J 3/02; G01J 3/0205; G01J 3/0218; G01J 3/10; G01J 3/2823; G01J 3/4406; G01N 21/6408; G01N 2201/0826; G01N 2201/0833; G02F 1/00; H03C 7/00

See application file for complete search history.

(56) References Cited

U.S. PATENT DOCUMENTS

| | | | | |
|---|---|---|---|---|
| 3,925,781 | A * | 12/1975 | Hulett et al. | 342/399 |
| 4,855,961 | A * | 8/1989 | Jaffe et al. | 367/7 |
| 5,000,568 | A * | 3/1991 | Trutna et al. | 356/73.1 |
| 5,127,405 | A | 7/1992 | Alcala et al. | |
| 5,447,159 | A * | 9/1995 | Schultz | 600/477 |
| 5,565,982 | A | 10/1996 | Lee et al. | |
| 5,865,754 | A * | 2/1999 | Sevick-Muraca et al. | 600/476 |
| 6,295,392 | B1 * | 9/2001 | Gregory et al. | 382/321 |
| 6,615,063 | B1 * | 9/2003 | Ntziachristos et al. | 600/312 |
| 2002/0065466 | A1 * | 5/2002 | Rather et al. | 600/447 |
| 2004/0082863 | A1 * | 4/2004 | McGreevy et al. | 600/476 |
| 2006/0106317 | A1 * | 5/2006 | McConnell et al. | 600/476 |
| 2007/0027391 | A1 | 2/2007 | Kohno et al. | |
| 2007/0038127 | A1 | 2/2007 | Goldstein et al. | |

OTHER PUBLICATIONS

Chen et al. "Time-resolved Optical Measurements with Spread Spectrum Excitation." Optics Letters. vol. 27, No. 20. Oct. 2002. pp. 1806-1808.*

(Continued)

*Primary Examiner* — Long V. Le
*Assistant Examiner* — Bradley Impink

(57) ABSTRACT

A system and method for optical lymph node mapping. The system is useful for guiding sentinel lymph node biopsy surgeries. A contrast agent that includes a fluorescent dye is injected near the site of a malignancy. The contrast agent drains into the lymphatic system, collecting in a sentinel node or nodes. The system utilizes one or more low-power continuous-wave lasers or light-emitting diodes modulated with a digital code sequence to probe the tissue suspected of containing the sentinel node. When the light is incident near the sentinel node, it will excite fluorescence from the dye. A portion of the scattered fluorescent light is captured with one or more photo-detectors. A correlation of the photo-detector signal and the digital code sequence is calculated to produce an estimate of the distribution of flight times for photons traveling from a given source to a given detector. The flight time distributions are used along with the measured amplitudes to reconstruct a map of contrast agent location within the tissue.

14 Claims, 7 Drawing Sheets

(56) References Cited

OTHER PUBLICATIONS

Gibson et al., "Recent Advances in Diffusion Optical Imaging," Phys. Med. Biology, vol. 50, R1-R43 (2005).
DeGrand et al., "An Opereational Near-Infrared Fluorescence Imaging System Prototype for Large Animal Surgery," Technology in Cancer Research and Treatment, vol. 2, No. 6, pp. 1-10 (2003).
Chen et al., "Time-resolved Optical Measurements with Spread Spectrum Excitation," Optical Letters, vol. 27, No. 20, pp. 1806-1808 (Oct. 15, 2002).
Hielscher et al., "Near-infrared Diffuse Optical Tomography," Disease Markers, vol. 18, 313-337 (2002).
Turconi et al. "Developments in Fluorescence Lifetime-based Analysis for Ultra-HTS," Drug Discovery Today, vol. 6, No. 12 (Suppl), pp. S27-S39, 2001.

* cited by examiner

METHOD AND APPARATUS FOR LYMPH NODE MAPPING

FIELD OF THE INVENTION

The field of the present invention pertains generally to optical imaging using near-infrared light, including more specifically, to the optical detection of sentinel lymph node location in order to guide surgical procedures.

BACKGROUND

Sentinel lymph node biopsy is a surgical procedure that involves removing a small sample of lymph tissue and examining it for signs of cancer. As an alternative to conventional full lymph node dissection, it is increasingly used as the standard of care in the staging of breast cancer and melanoma. The sentinel lymph node (SLN) is the first node, or group of nodes, in the lymphatic network to come into contact with metastatic cancer cells that have spread from the primary tumor site. SLN biopsy allows a physician to obtain information about the other lymph nodes in the network without exposing the patient to the risks of conventional surgery. Further surgery to remove other lymph nodes may be avoided if no cancer cells are found in the sentinel lymph nodes.

SLN biopsy usually begins with the injection of a radioactive tracer (technetium-99 sulfur colloid), a blue dye, or both into the area around the original cancer site. Lymphatic vessels carry the tracer to the sentinel node (or nodes); this is the lymph node most likely to contain cancer cells. Prior to surgery, a wide field-of-view gamma camera is typically used to image the location of the radiotracer. Images are generally taken from multiple positions and perspectives, resulting in a map of the drainage pattern of lymphatic fluid from the skin to the lymph nodes. By showing where the cancer is likely to have spread, the map enables the surgeon to plan the full procedure prior to the first incision. During surgery, the surgeon achieves further guidance either through direct visualization of the injected blue dye or by detecting the radioactive tracer with a hand-held gamma probe. After surgery, the lymph node is sent for pathological examination that can include microscopic inspection, tissue culture, or immunological tests.

The current approach of using radioisotopes for SLN mapping has several drawbacks. First, while the radiation risk to patients and medical practitioners is relatively low compared to other medical procedures, the handling of radioisotopes still requires special precautions. Second, the procedure requires the coordination of both surgical and nuclear medicine personnel, resulting in both scheduling issues and increased cost. Lastly, the time required for the radiotracer to travel through the lymphatic system can be as long as several hours. It is highly desirable to have an alternative system that could be used without radiotracers and that a surgeon could utilize without the involvement of other specialists. It is also desirable to have a system that uses a contrast agent with more rapid kinetics.

Diffuse optical imaging techniques are known in medical and biological applications. Overviews of diffuse optical imaging techniques can be found in "Recent Advances in Diffusion Optical Imaging" by Gibson, et al, Phys. Med. Biology, vol. 50 (2005), R1-R43 and in "Near-infrared Diffuse Optical Tomography," by Hielscher, et al, Disease Markers, Vol. 18 (2002), 313-337. Briefly, diffuse optical imaging involves the use of near-infrared light incident upon a sample of interest. An example in the medical and biological field is optical mammography where near infrared light is used to illuminate breast tissue. A detector is placed on the opposite side of the breast from the incident light some distance away and collects scattered light from the breast tissue. The scattered light of interest that is detected may be directly scattered incident light or scattered fluorescence light caused by the excitation of an injected fluorescing material that fluoresces when exposed to the incident light. By measuring the amplitude of the light of interest at the detector and the distribution of photon arrival times at the detector for various source and detector positions, a reconstruction of the underlying tissue optical properties can be made. An overview of image reconstruction techniques can be found in the citations given in the aforementioned review articles.

Measurements of the photon flight-time distributions are typically carried out using either a time-domain or a frequency-domain technique. In the time-domain technique, the sample is excited with pulse of light from a pulsed laser and the scattered light is measured using a detector with single-photon sensitivity. The detector measures the time delay between the excitation pulse and the first detected photon. The flight-time distribution is determined by using many repeated pulses and building up a histogram of the measured time delays. Unfortunately, the pulsed laser sources and single-photon detectors are relatively expensive. Because detection is typically done at the single-photon level, it can require a significant amount of time to build-up enough data to approximate the flight-time distribution. One disadvantage of the frequency-domain approach is that it is not a direct measurement of the photon flight time. Rather, it provides an estimate of the mean flight time based on the phase shift between a detected signal and the excitation signal. In some cases, more accurate image reconstructions can be obtained using more complete measurements of the flight-time distributions. This data is not readily obtained with frequency-domain instrumentation. A further disadvantage of the frequency-domain approach is the need for accurate high-frequency analog electronics. An overview of both the time-domain and frequency-domain techniques can be found in the above-referenced article by Hielscher, et al.

U.S. Pat. No. 5,565,982 discloses a time-resolved spectroscopy system using digital processing techniques and two low power, continuous wave light sources. The disclosed system requires two light transmitters of different wavelengths modulated with separate codes for interrogating a sample of interest. Properties of the sample are inferred by differential comparison of the return signals from each of the two light sources. It is undesirable to have two distinct light sources due to the cost and complexity involved. Furthermore, the noise level associated with a measurement made with two separate light sources will be higher than with a single source even if the codes used to drive the two sources are orthogonal. It is desirable to have a means of interrogating a particular tissue volume with a single light source at one wavelength in order to obtain temporal information.

What is needed is an imaging system capable of sentinel lymph node mapping that does not require the use of radiotracers. Furthermore, the system should be implemented with low-power continuous-wave light sources and digital electronics.

SUMMARY OF THE INVENTION

The inventions presented herein provide for direct measurements of photon flight-time using any light source modulated with a known digital pattern. A preferred system uses a low-power continuous-wave light source and low-cost detector. Preferably the measurement system is implemented with digital electronics. One embodiment of the system and methods disclosed comprises a continuous-wave light source modulated with a digital waveform for interrogating a tissue volume, a photo-sensitive detector for measuring the scattered light from the sample, and electronics for sampling the detector output and performing a correlation of the output signal with the modulation waveform. Other embodiments include electronics and software for calculating the parameters of the flight-time distribution from the measured correlation. The inventions further comprise a system with multiple sources for interrogating different sections of tissue volume, multiple detectors for detecting light scattered by the different sections of tissue volume, and software means for converting the detected signals into a reconstructed image of the underlying volume. Another embodiment includes a means of imaging the location of fluorescent dye within tissue in order to construct a map of the lymph nodes.

DETAILED DESCRIPTION OF THE DRAWINGS

Figure 1:
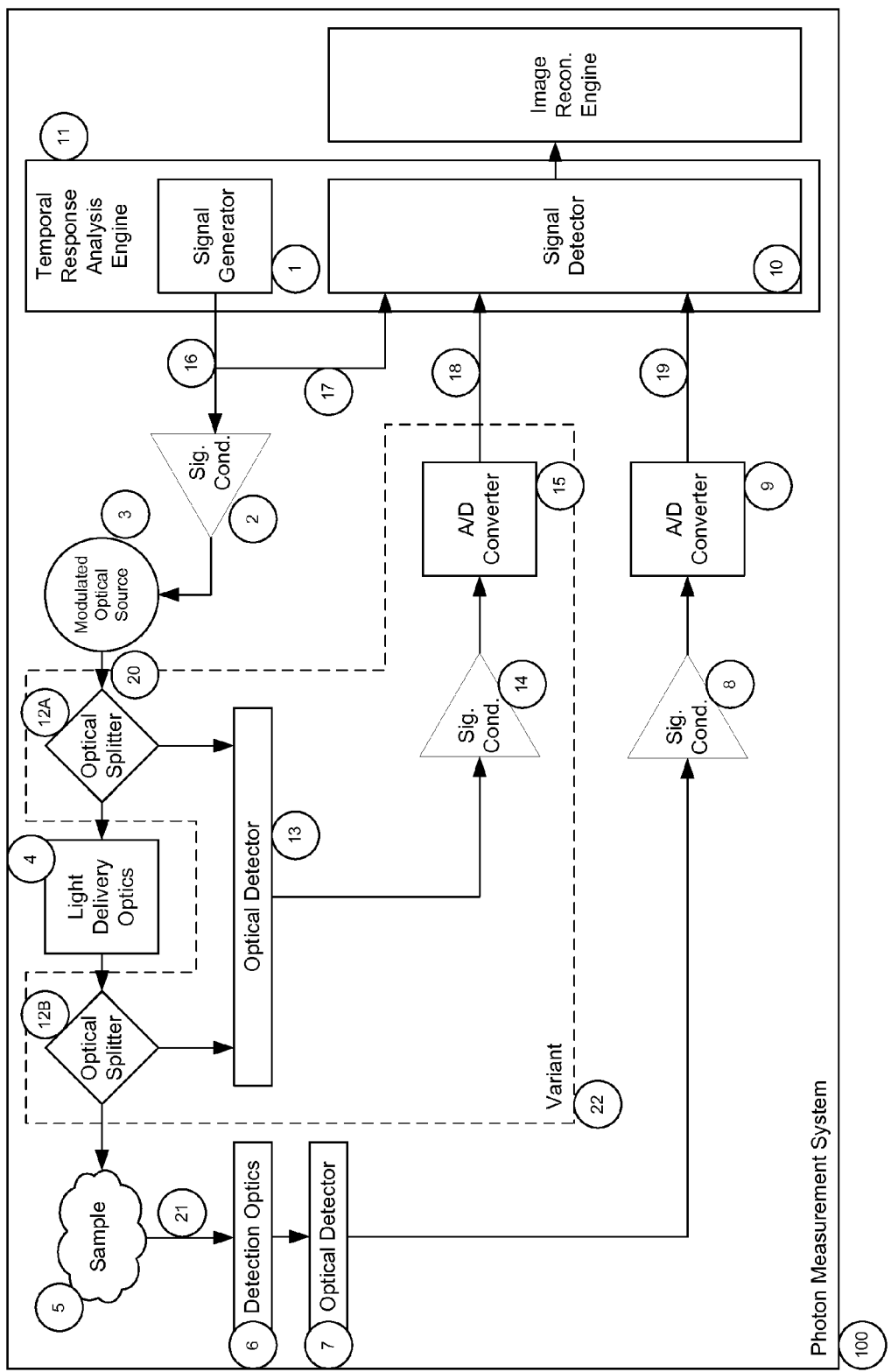
FIG. 1 is a functional block diagram of the major components of a preferred photon measurement system of the present invention.

A functional block diagram of a preferred photon measurement system 100 is depicted in FIG. 1. The photon measurement system can be used to measure the interaction of photons with a sample 5. In certain applications, the sample 5 may be human breast tissue or fat tissue but it could just as well be any semitransparent material. The photon measurement system 100 preferably includes Temporal Response Analysis Engine 11. The Temporal Response Analysis Engine 11 generates a digital modulation signal for driving an illumination light source that is used to interrogate the sample. The Temporal Response Engine 11 also provides a means for processing a detected optical signal from the sample 5 to extract information about the sample 5. Preferably a digital modulation signal 16 is generated in the signal generator 1 and transmitted to the transmit signal conditioner 2. The digital modulation signal 16 is the digital representation of a chosen code sequence. The code sequence is preferably chosen from the known pseudorandom binary sequences (PRBS), Gold codes, Golay codes, Kasami codes, Walsh codes, or other codes that possess the preferred desirable property of large auto-correlation values and low cross-correlation values. The digital modulation signal 16 may represent a single code pattern or multiple repeats of the same pattern. A single complete set of code patterns is designated a modulation frame or code pattern frame. The digital modulation signal 16 is preferably transmitted to the signal detector 10 as an electronic reference signal 17. The transmit signal conditioner 2 formats the digital modulation signal 16 as necessary to drive an optical illumination source 3. In the preferred photon measurement system 100, the modulated optical source is a 785 nm diode laser made by Hitachi Corp. Formatting of the digital modulation signal 16 in the preferred embodiment involves converting the digital modulation signal 16 to an analog voltage waveform that is coupled through a 50-ohm bias-T to the DC drive current of the optical illumination source 3. In other embodiments, the optical illumination source 3 may be a different laser diode, a light-emitting diode, or a light source used together with an external optical modulator. The optical illumination source 3 generates the modulated optical wave 20 which is preferably transmitted to the sample 5 by light delivery optics 4. The preferred light delivery optics 4 is a 3 mm diameter fiber bundle located between the optical illumination source 3 and the sample 5 to deliver the modulated optical wave 20 from the optical illumination source 3 to the sample 5. In other embodiments the light delivery optics 4 comprises other arrangements of optical fibers, lenses, mirrors or other optical delivery components. When the modulated optical wave 20 illuminates the sample 5 scattered optical waves 21 are generated. In the preferred photon measurement system, the sample 5 is treated with a fluorescent material that will fluoresce when it is illuminated by the modulated optical waves 20. In the preferred system the scattered optical waves 21 are fluorescence generated from a fluorescent material within the sample 5. The fluorescent material is preferably an exogenous contrast agent injected into the sample 5 or alternatively it is preferably some constituent component of a material that exhibits endogenous fluorescence. The detection optics 6 are situated so that a portion of the modulated optical waves 21 are detected by the detection optics 6. In the preferred photon measurement system 100, the detection optics 6 include an optical filter for separating the fluorescing scattered optical waves 21 from the modulated optical waves 20. The optical filter preferably transmits the higher wavelength fluorescence and blocks the lower wavelength illumination light. In applications where the scattered optical waves 21 of interest are not fluorescing, an optical filter is not required.

In the preferred photon measurement system 100, the detection optics 6 preferably include a second 3 mm diameter fiber bundle located between the optical filter and the optical detector 7. The optical detector 7 converts the scattered optical waves 21 to an electronic signal. In the preferred photon measurement system 100, the optical detector 7 is preferably a photomultiplier tube, model R7400U-20 from Hamamatsu Corp. In other embodiments, the optical detector 7 may be a PIN photodiode, an avalanche photodiode, a charge-couple device, or other suitable photosensitive element. As previously stated, the optical detector 7 preferably converts detected scattered optical waves 21 into an electronic signal which is communicated to the detected signal conditioner 8. The detected signal conditioner 8 preferably formats the signal so it may be converted to discrete samples by an Analog to Digital (A/D) converter 9. The A/D converter 9 outputs a detected response signal 19. The detected response signal 19 is communicated to a signal detector 10, where it is preferably correlated with the electronic reference signal 17 to extract a sample transfer characteristic.

Information about the temporal properties of the photons is preferably calculated from the sample transfer characteristic. This information preferably includes such properties as direct measurements of photon time-of-flight and the fluorescence lifetime. The estimate of photon times-of-flight is then preferably used to estimate characteristics of the tissue such as the absorption coefficient, scattering coefficient, or location of fluorescing material.

Another embodiment of the photon measurement system 100 includes an optical reference generator 22. The optical reference generator 22 preferably includes an optical splitter 12A or 12B that routes a portion of the modulated optical wave 20 to a secondary optical detector 13. The position of the optical splitter 12A or 12B can be either before or after the light delivery optics. The output of the secondary optical detector 13 is preferably routed to a secondary signal conditioner 14 whose output is communicated to a secondary A/D converter 15. The secondary A/D converter 15 preferably outputs a source reference signal 18 which can be correlated with the detected response 19 to extract the sample transfer characteristic. Using the source reference signal 18 as opposed to the electronic reference signal 17 allows the filtering of the temporal properties of the signal conditioner 2 and the modulated optical source 3 from the measured transfer characteristic.

Figure 2:
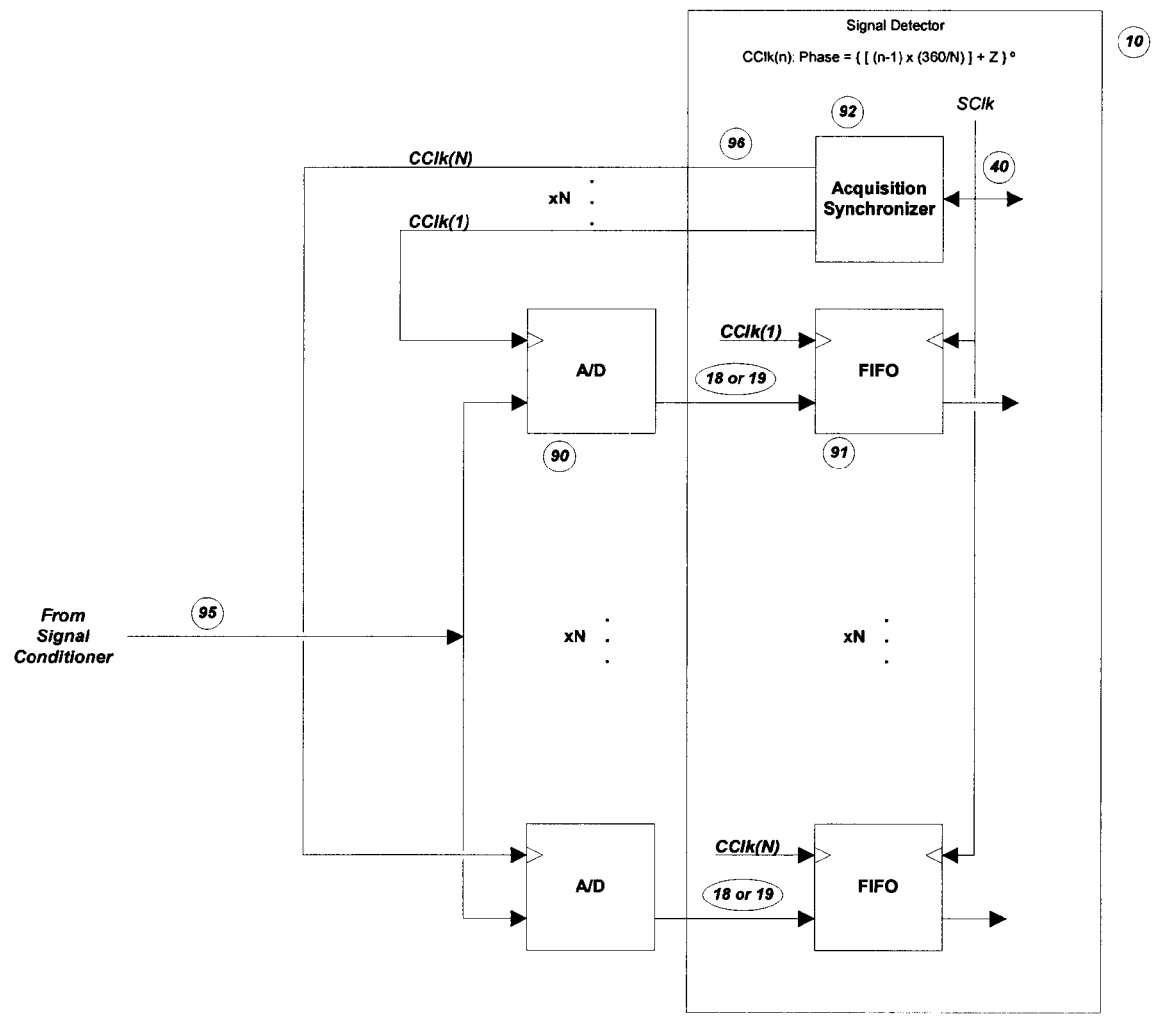
FIG. 2 is a diagram of preferred Analog-to-Digital converters and their interface to the signal detector.

The preferred hardware implementation of the A/D converter module and its interfaces to the signal detector 10 are shown in FIG. 2. An array of N A/D converters 90 preferably receives the analog signal 95 in parallel from the signal conditioner 8 or 14. The output samples 18 or 19 from the A/D converters 90 are preferably communicated to the First-In-First-Out buffers (FIFOs) 91 where they are buffered for distribution to the internal components of the signal detector 10. In the preferred photon measurement system the A/D converters 90 are eight MAX 108 integrated circuits made by Maxim operating at 250 Msample/sec and outputting two data samples at a time in parallel at 125 MHz. The FIFOs 91 are preferably implemented within a Xilinx 4 FPGA. The acquisition synchronizer 92 preferably controls signal acquisition and digital data distribution through the conversion clock (CClk) signals 96.

The acquisition synchronizer 92 is preferably synchronized with an externally provided synchronization clock (SClk) 40 which is also preferably used to synchronize the signal generator 1. The signals CClk[1 ... N] are preferably generated within the acquisition synchronizer 92 and preferably have the same frequency as SClk 40 but are offset in phase from SClk 40 in N fixed increments of $(360 \div N)°$, with the phase of CClk[1] set to the fixed offset of $Z°$. In the preferred system the internal clock generation capabilities of the Xilinx FPGA are used to implement the acquisition synchronizer 92 directly. The A/D converters 90 preferably perform their conversions in sync with the conversion clocks 96 such that they generate samples at N discrete sample times spread evenly throughout the fundamental sample interval defined by the period of SClk 40. The effective sample rate for the array of converters is preferably N times the rate defined by SClk 40. This process of using multiple A/D converters sampling out of phase to increase the effective sample rate is what we call parallel over-sampling. In the preferred photon measuring system, parallel over-sampling results in an effective sample rate of 2 Gsamples/sec. The offset value Z allows the entire sample set to be offset by some phase from the synchronization clock 40. The acquisition synchronizer 92 preferably is configured such that the value of Z can be varied synchronously with the modulation frame, or with a block of frames called a frame block. This allows Z to follow a sequence of K values smaller than $(360 \div N)°$ such that on successive modulation frames/frame blocks the effective sampling phases (relative to the synchronization clock) take on K values intermediate to those created by the N conversion clocks in any given frame. In this case preferably the input signal at any given A/D converter 90 will be sampled at K discrete phases over K blocks. The detected response 19 is preferably assumed to be stationary with respect to the start of the code pattern block over that time interval. The preferred K discrete sampling phases correspond to K discrete sample times and the effective temporal resolution of the sampling process is preferably increased by a factor of K. This process is referred to as temporal over-sampling.

In the preferred photon measuring system the value of Z is always zero and temporal over-sampling is achieved by adjusting the phase of the modulation as described below rather than by adjusting the phase of the A/D converter sampling. Preferably the FIFOs latch input data to the A/D converters 90 synchronously with the corresponding conversion clock 96. The FIFO 91 output data is preferably provided to the internal components of the signal detector 10 synchronously with the synchronization clock 40 such that all further processing is synchronized with the synchronization clock 40.

Figure 3:
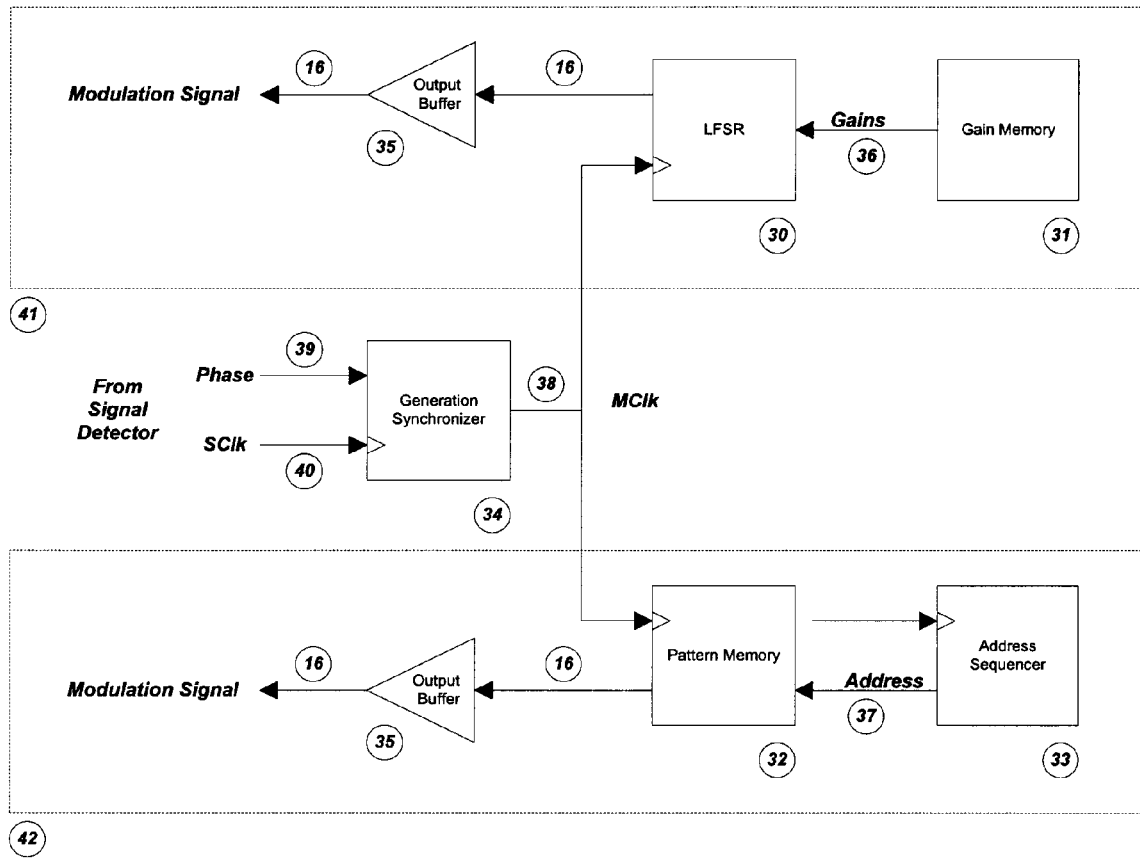
FIG. 3 is a functional block diagram of a preferred signal generator.
Figure 4:
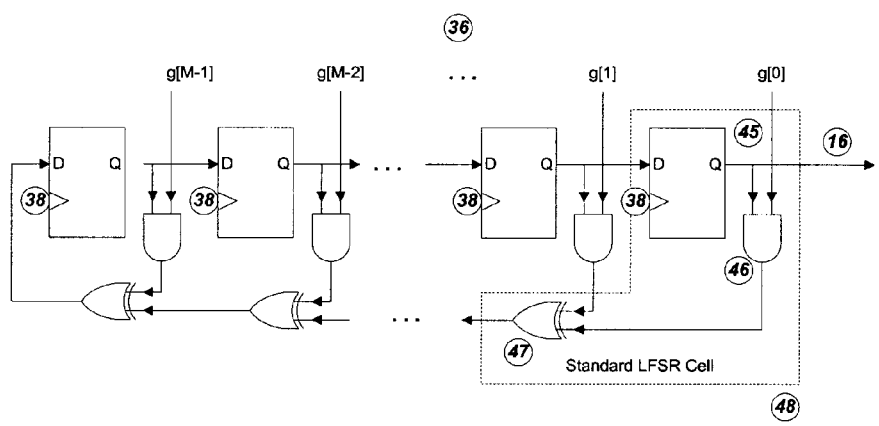
FIG. 4 depicts an implementation of a preferred Linear Feedback Shift Register.
Figure 5:
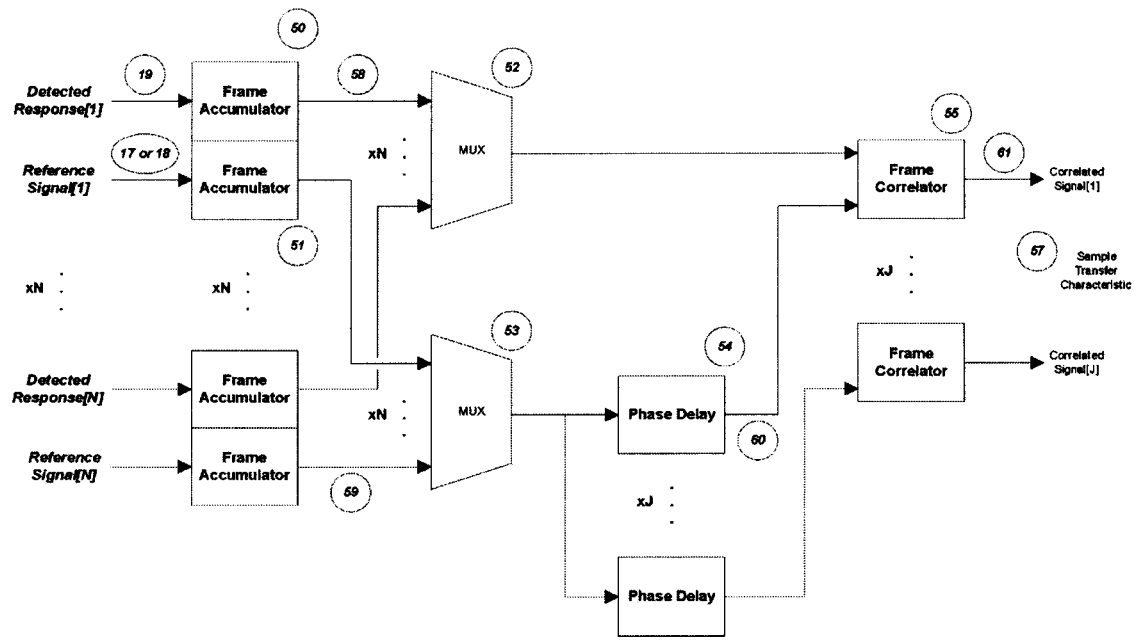
FIG. 5 is a functional block diagram of a preferred signal detector.
Figure 6:
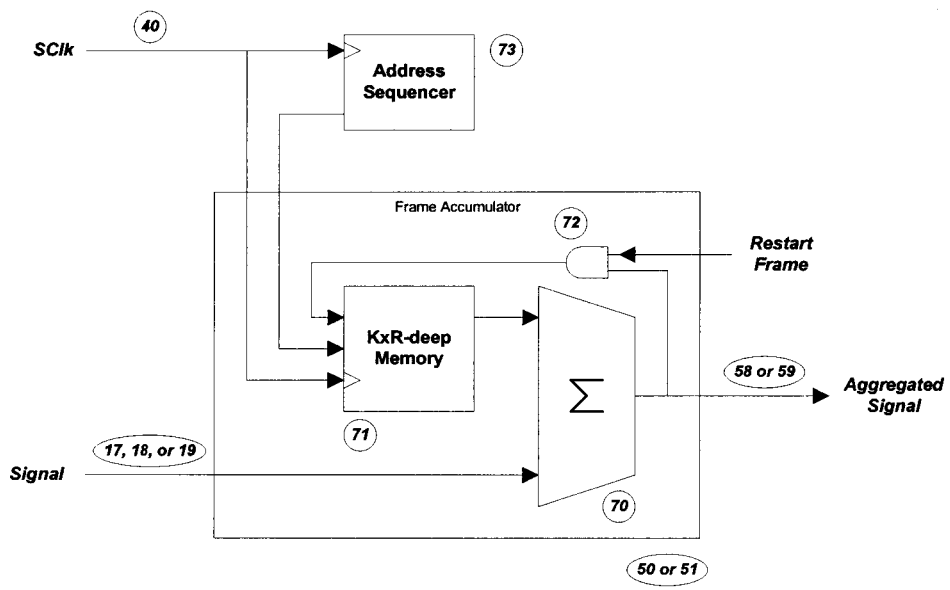
FIG. 6 is a functional block diagram of a preferred frame accumulator.
Figure 7:
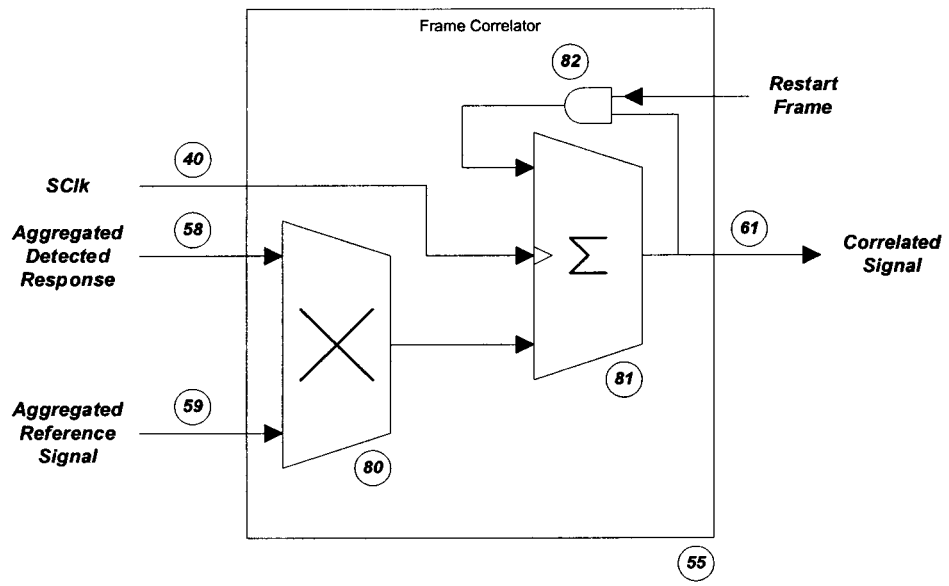
FIG. 7 is a functional block diagram of a preferred frame correlator.

The preferred implementation of the Temporal Response Analysis Engine 11 are shown in FIGS. 3 through 7; the preferred signal generator 1 is shown in FIGS. 3 and 4, while the preferred signal detector 10 is shown in FIGS. 5, 6, and 7. In the preferred system the Temporal Response Analysis Engine 11 is implemented as logic blocks within a Xilinx 4 FPGA.

The functional blocks of the preferred signal generator 1 are shown in FIG. 3. The top 41 and bottom 42 signal paths are two preferred variants for generating different code patterns for the modulation signal 16. In the top path 41 a Linear Feedback Shift Register (LFSR) 30 is preferably used to create a PRBS code. The specific code pattern is preferably determined by the number of state bits within the LFSR 30 and the gain code 36 input to the LFSR 30. In one preferred implementation the gain code 36 is stored in a gain memory 31, which is preferably configured to allow the code pattern 16 to be changed during operation either by selecting one of several gain codes from a read-only memory or by setting a new gain code into a writable memory. In other embodiments the gain code 36 may be hard-wired into the LFSR 30, or a code-specific state-machine designed to generate a desired code through a series of state transformations may be used in place of the LFSR 30. In the bottom path 42 the entire code pattern is preferably stored as a bit sequence in a pattern memory 32. The sequence in which pattern bits are presented is preferably determined by an address sequencer 33 which preferably provides the cell addresses 37 for the memory. The address sequencer 33 is preferably configured to allow changing the code pattern 16 during operation either by selecting one of several patterns stored in a read-only memory or by inputting a new pattern into a writable memory.

The modulation signal 16 for both the LFSR 30 or pattern memory implementation is preferably buffered by an output buffer 35 to make the signals 16 more robust when driving external components. Timing for presentation of the code pattern bits is preferably controlled by a generation synchronizer 34 which preferably generates the master clock (MClk) 38 for the LFSR 30 and the address sequencer 33. The master clock 38 is preferably synchronized to a system synchronization clock (SClk) 40 which preferably controls both code pattern generation and response signal acquisition. MClk 38 preferably operates at the same frequency as SClk 40 but is preferably offset in phase by an amount specified by the phase input 39, which is preferably an externally programmable parameter. This phase offset allows the relative phase between the modulation signal 16 and the detected response 19 to be adjusted. If the phase is adjusted by some increment, (360÷K)°, at the end of each code pattern block or set of blocks the detected response resulting from the modulation signal will preferably be sampled at K discrete phases over K blocks. In this embodiment of the photon measuring system as with the preferred embodiment, the detected response 19 is assumed to be stationary with respect to the start of the code pattern block over that time interval so that the K discrete sampling phases correspond to K discrete sample times and the effective temporal resolution of the sampling process is increased by a factor of K.

This temporal over-sampling is functionally equivalent to the technique described for temporal over-sampling in the A/D converter embodiment. In other embodiments the external phase specification may represent the phase increment rather than the absolute phase, and the generation synchronizer 34 may increment the phase internally.

The preferred implementation of the LFSR 30 is shown in FIG. 4. The LFSR 30 is preferably a state-machine comprising M standard LFSR cells 48 which hold and transform the state. The LFSR cells 48 are preferably linked in a numbered sequence, and the output from the LFSR 30 is the current state of cell number zero. Each cell preferably comprises a state latch 45 which holds a single bit of state information, a gain element 46 to control the feedback gain for the cell based on the externally provided gain code 36, and an accumulator 47. The accumulator 47 preferably adds the feedback from the cell to the cumulative feedback from all previous cells. At each clock increment the state for a cell is updated to match the previous state from the next higher cell in the chain; the state of the last cell in the chain is updated with the accumulated feedback from all the previous cells. The accumulator 47 for the last cell in the chain may be omitted if desired. The pattern generated by the LFSR 30 is preferably determined by the number of cells in the chain and by the gain code. In a preferred embodiment the gain code is provided from an external source to allow the code pattern to be modified. In other embodiments the gain code may be a fixed value. In embodiments in which the gain code is fixed, the implementation of the gain elements and accumulators for each cell may be optimized for the specific gain code for that cell rather than implemented in the generalized fashion shown. The clock for the LFSR 30 and for all its internal latches is preferably the signal generator master clock 38.

The preferred functional blocks for the signal detector 10 are shown in FIG. 5. The detected response 19 and either the electronic reference signal 17 or the source reference signal 18 are received at two frame accumulators 50 and 51, where the samples for each discrete sample time are accumulated with samples from identical sample times from different modulation frames to form the aggregated detected response 58 and the aggregated reference signal 59. As a result of this aggregation, the effective data rate at which samples are preferably processed in following blocks is reduced by a factor equal to the number of frames aggregated into each sample point. The frame accumulators 50 and 51 are preferably replicated N times to handle the N channels of the A/D converter independently. The internal details of the frame accumulators 50 and 51 for the detected response and the reference signal may differ, depending on the digital format of the two signals. For example, if the reference signal used for analysis is the electronic reference signal 17 rather than the source reference signal 18 its value for each sample time is known a priori to be identical for every frame and to take on only two possible binary values, 0 or 1. In that case preferably the frame accumulator 51 for the reference signal 17 need only store one bit per sample time, equal to the value of the modulation signal for that sample time. At some point between the output of the frame accumulators and final output of the sample transfer characteristic 57 the N acquisition/accumulation channels are preferably re-interleaved into a single data stream. In one preferred embodiment two multiplexers 52 and 53 perform this reintegration at the output of the frame accumulators 50 and 51. In other embodiments this re-integration may take place at any other desired point in the signal processing chain. With or without re-integration the aggregated detected response 58 and the aggregated reference signal 59 are routed to the frame correlator 55 where the two signals 58 and 59 are preferably combined by a cross-correlation algorithm to produce the correlated signal 61 which preferably comprises a single value for each complete aggregated frame of samples. The correlated signal 61 represents the degree to which the aggregated response signal 58 contains components matching the aggregated reference signal 59. If the aggregated reference signal 58 is delayed by a time τ before presentation to the correlator 55 then the correlated signal 61 represents the degree to which the aggregated response signal 58 contains components of the delayed version of the reference signal 60. The sample transfer characteristic 57 comprises a set of correlated signals calculated for a range of J such delay times. Phase delay blocks 54 generate the delayed versions of the aggregated reference signal 60. For simplicity the J phase delay blocks 54 are illustrated as discrete components operating in parallel and each providing the complete delay required for one correlated signal. In one preferred embodiment they comprise a cascade of J phase delay blocks each providing the time increment between one correlated signal and the next. The phase delays for the correlated signals are preferably discrete and correspond to integral multiples of the synchronization clock 40 period. The phase delay blocks 54 are preferably implemented as shift registers or FIFOs of the appropriate depth and clocked by the synchronization clock 40. In other embodiments the time delay may be implemented using other methods. In one preferred embodiment each phase delay is processed by a corresponding frame correlator 55. In other embodiments a single frame correlator 55 may be used to calculate the correlated signal 61 for multiple phase delays by presenting the detected response data to its input multiple times, using a different phase delayed version of the reference signal 60 for each iteration. In this case fewer frame correlators 55 are required.

The details of the preferred frame accumulator 50 or 51 are shown in FIG. 6. Samples from the signal 17, 18, or 19 are preferably accumulated in the adder 70 by summing them with values taken from the memory 71; the resulting aggregated signal 58 or 59 is routed to the output of the accumulator and stored back into the memory at the same location from which the original data was taken. Each discrete sample time for the channel is represented by a single addressed cell within the memory. The size of the memory is preferably determined by two parameters, K and R, which preferably encode the sampling scheme. K represents the number of discrete phases at which samples are preferably taken in various frames during temporal over-sampling. R is the ratio of the number of samples in a modulation frame to the number of sampling channels provided in the A/D converter 90 for parallel over-sampling and signifies the number of samples that must be accommodated by each channel within a single frame. A preferred sample enable gate 72 is provided to restart the accumulation process at the beginning of each set of frames by clearing the cells in the memory. The address sequencer 73 selects the cell of the memory to be addressed for each sample point. The frame accumulators 50 or 51 preferably run synchronously with the synchronization clock 40 (although out of phase), so only a single address sequencer is required to address all the frame accumulators.

The details of the preferred frame correlator 55 is shown in FIG. 7. The ideal method for correlating the signals is to take the integral of the detected response 19 weighted by the reference signal 17 or 18. Because the preferred embodiment is a sampled system the integration is approximated by summation over all the samples within a frame set using the adder 81 to generate the correlation signal 61. The weighting of the aggregated detected response 58 by the aggregated reference signal 59 is preferably performed by a multiplier 80. Other embodiments may employ other weighting and integration schemes, including scaling and integration in the analog domain directly on the detected signals. A sample enable gate 82 is preferably provided to restart the accumulation process at the beginning of each set of frames by clearing the correlator.

Figure 8A:
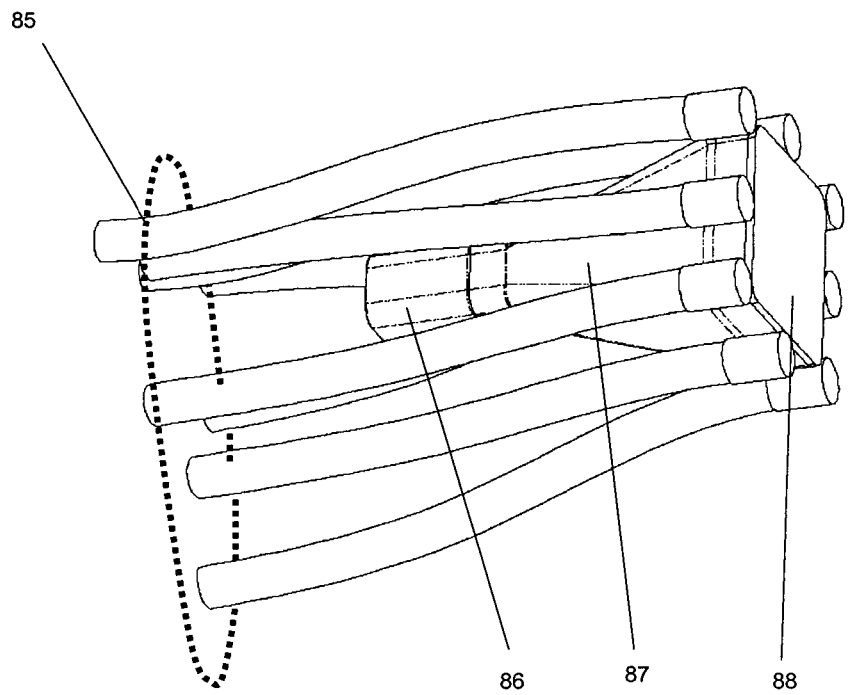
FIGS. 8A and 8B depict an embodiment of the present invention using a 64-element fphotomultiplier array.
Figure 8B:
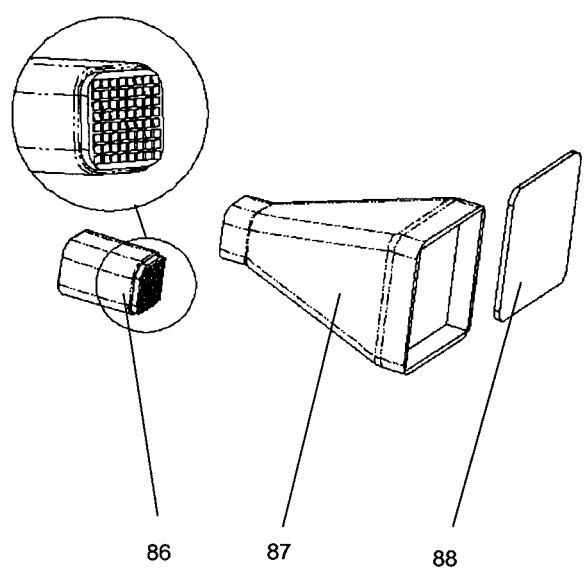
Figure 9:
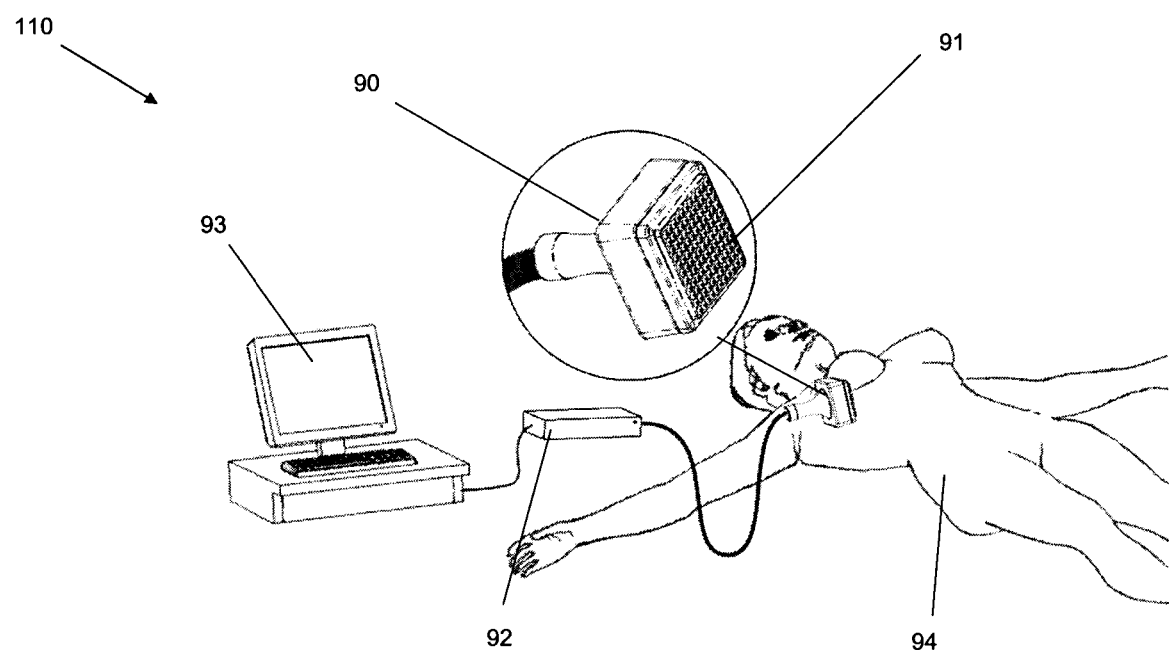
FIG. 9 is an embodiment of the present invention using an 11×11 array of fibers to deliver light between the sources or detectors and the patient.

The photon measurement system 100 is useful for interrogating a section of tissue located generally between the light delivery optics and the detection optics. In order to interrogate a larger tissue volume, it is useful to have a system where the photon measurement system is replicated so that separate tissue sections can be interrogated with separate source-detector pairs. One embodiment of such a system is shown in FIGS. 8A and 8B. Eight fiber bundles 85 are used to deliver light from eight different sources to the tissue. The fiber bundles are shown encircled by the dotted line in FIG. 8A. The detectors are a 64-element photomultiplier array 86 manufactured by Hamamatsu with the individual elements in an 8×8 arrangement. Fluorescent light from the tissue passes through an optical filter 88 that blocks light at the excitation wavelength. The fluorescent light is coupled to the detector array by a 2.5:1 tapered imaging fiber bundle 87 made by Schott Corp. An exploded view of the detector array 86, filter 88, and imaging fiber bundle 87 is given in FIG. 8B. Each source-detector pair can be coupled to electronics as shown functionally in FIG. 1 to form an individual photon measurement system. Each source-detector pair yields information about photon time of flight through a somewhat different section of tissue than any other pair. Each source can be turned on sequentially, while all the detectors can be sampled simultaneously while a given source is on. Alternatively, each source can be driven with a different code such that any code is orthogonal to the others. In this case, the sources can be driven simultaneously and the low cross-correlation of the respective reference signals allows separation of the signals. The sequential case will exhibit improved signal-to-noise ratio compared to the simultaneously on case due to the non-ideal cross-correlations obtained in practice. Another embodiment of the present invention is shown in FIG. 9. In this case, the imaging instrument 110 includes an 11×11 array 91 of multimode fibers for coupling light from the sources and detectors in an electronics module 92 to the tissue. Each fiber can be coupled to either a source or a detector. The fibers are spaced at 1 cm intervals on the imaging head 90. The image reconstructed from the measured data is displayed on the monitor 93. The imaging head 90 can easily be manipulated to image various parts of the patient 94. The present invention is not limited to the particular geometries described here. The use of the photon measurement system 100 is possible with various combinations of sources and detectors and various positions of the sources and detectors. In the examples described, the geometry is a reflection geometry with the sources and detectors effectively on the same side of the tissue. In other embodiments, the detection optics can be placed on the opposite side of the tissue from the light delivery optics. The particular number of sources and detectors can also be varied depending on the resolution and field-of-view required for a particular application. In the present embodiments, the instrument is intended to cover an area of approximately 10 cm×10 cm area. Imaging a larger area can be accomplished by moving the instrument head across the area. The embodiments described utilize a photomultiplier array as the optical detectors. In other embodiments, it is possible to use PIN photodiodes, avalanche photodiodes, individual photomultiplier tubes, detector arrays, charge-coupled device arrays, or other photosensitive elements.

The present invention is utilized for sentinel lymph node mapping as presently described. A patient is injected near the site of a malignancy with a dye that fluoresces when exposed to near-infrared light. In particular, indocyanine green (ICG) can be excited at wavelengths around 785 nm and fluoresces at wavelengths around 830 nm. The dye serves both as a visual guide for the surgeon and as a contrast agent for the optical imaging system. ICG has the advantage that it is already approved for use in medical procedures such as angiography; however, several alternative contrast agents are also available. Imaging proceeds as follows. Assuming the imaging is performed reasonably soon after injection of the dye, the dye will be relatively well-localized in the sentinel node or nodes. If the dye is ICG, this amount of time is one the order of minutes. The imaging head is placed in contact or in close proximity to the tissue suspected of containing the sentinel node. The correlator output, or characteristic transfer function, is measured for each source-detector pair. For any given source and detector position, it is possible to calculate a priori the expected characteristic transfer function for a given location of fluorescence dye. In practice, because the tissue is so highly scattering, neighboring source-detector pairs can have somewhat overlapping interrogation regions. The image reconstruction problem consists of estimating the most likely distribution of dye given all the measurements of characteristic transfer functions from all the source-detector combinations. Various techniques are known for performing such an inversion problem, including such methods as singular-value decomposition and the Algebraic Reconstruction Technique, also known as the Gauss-Seidel method. The result of the inversion is a volumetric map of the location of dye within the tissue. Because the dye collects predominantly in the sentinel node(s), this map is effectively a map of the sentinel node location. This map is displayed in the form of an image or images on a monitor attached to the instrument. The surgeon uses this image to plan his surgical incisions. The estimated positions of the sentinel node with respect to the instrument are also displayed on the monitor, allowing the surgeon or other operator to mark the body before the surgery begins.

A preferred imaging method for locating the sentinel lymph node or nodes is as follows. The patient is injected with fluorescent material near the site of a malignancy. Imaging begins after an amount of time sufficient for the fluorescent material to reach the sentinel lymph node or nodes. The instrument head is placed over the patient at a position that represents an initial estimate for the location of the sentinel node. With the instrument head in position, the first optical source is turned on for an amount of time corresponding to the desired number of repeats of the code sequence. Scattered optical waves are measured at each corresponding detector. The output of each detector is correlated with the reference signal as described above to produce a temporal transfer characteristic corresponding to the source-detector combination. The temporal transfer characteristics for each source-detector combination are stored in memory. The process is repeated for each subsequent optical source until temporal transfer characteristics are collected for all desired source-detector pairings. The acquired temporal transfer characteristics are then used to reconstruct an image of the underlying tissue volume using an algorithm implemented in software. The algorithm is based on the ability to estimate a priori the temporal transfer characteristic that will be obtained for any source-detector pairing for any particular location of fluorescent dye. The algorithm generates a most likely estimate of the fluorescent material locations based on the a priori models given the measured temporal transfer characteristics. This estimate of fluorescent material locations is displayed in the form of a volumetric image on a monitor connected to the instrument. The user of the instrument can conclude based on the image whether or not the underlying tissue contains a sentinel node. Generally, the node will be imaged as a subset of the volume with a high estimated concentration of fluorescent material. If the user judges that the sentinel node has been located, he may physically mark the body where the instrument head had been placed with a pen to indicate the area in which to cut. Alternatively, he may save the image on the screen or on a printout so that it may be referred to during surgery. If the user concludes that the sentinel lymph node has not been located, he moves the instrument to a different location and the process is repeated.

The invention claimed is:

1. A sentinel lymph node imaging system comprising:
at least one modulated optical source configured to generate a modulated optical wave modulated according to a Golay code sequence;
a code selector configured to provide said Golay code sequence to the modulated optical source, the code selector comprising an address sequencer and a pattern memory for storing a plurality of Golay code sequences, wherein the address sequencer is configured to allow changing the Golay code sequence by selecting one of several patterns stored in the pattern memory or inputting a new code sequence into the pattern memory;
delivery optics coupled to the at least one modulated optical source configured to direct the modulated optical wave at a mammal whose sentinel lymph nodes are to be imaged;
a first photo-sensitive detector configured to detect fluorescent light emitted from a fluorescing material injected into said mammal whose sentinel lymph nodes are to be imaged;
an optical splitter coupled to the delivery optics to direct the modulated optical wave to a second photo-sensitive detector;
digital detector electronics coupled to said first photo-sensitive detector and to said second photo-sensitive detector configured to sample a first detector output from said first photo-sensitive detector and a second detector output from said second photo-sensitive detector, and further configured to perform a correlation of said first detector output with said second detector output, and to generate a temporal transfer correlation signal reflecting photon time-of-flight characteristics from said at least one modulated optical source; and
an image reconstruction engine coupled to said digital detector electronics configured to reconstruct an image of an underlying tissue volume and sentinel lymph nodes based in part on the temporal transfer correlation signal.

2. The node imaging system of claim 1 wherein the first photo-sensitive detector comprises a plurality of detector elements.

3. The node imaging system of claim 1 wherein the first photo-sensitive detector comprises an array of detectors.

4. The node imaging system of claim 1 wherein said first selected Golay code sequence has multiple repeats of the same pattern.

5. The node imaging system of claim 1 wherein said digital detector electronics is configured to utilize temporal over-sampling.

6. The node imaging system of claim 1 wherein said image reconstruction engine is configured to use an inversion technique.

7. The node imaging system of claim 6 wherein said inversion technique is singular-value decomposition.

8. The node imaging system of claim 6 wherein said inversion technique is Algebraic Reconstruction Technique.

9. A sentinel lymph node imaging system comprising:
a plurality of separate optical source-detector pairs for interrogating separate tissue sections;
wherein each source-detector pair includes a modulated optical source configured to generate a modulated optical wave modulated according to a Golay code sequence;
a code selector configured to provide said Golay code sequence to each modulated optical source, the code selector comprising an address sequencer and a pattern memory for storing a plurality of Golay code sequences, wherein the address sequencer is configured to allow changing the Golay code sequence by selecting one of several patterns stored in the pattern memory or inputting a new code sequence into the pattern memory such that each modulated optical source can be driven with a different Golay code sequence;
delivery optics coupled to each modulated optical source configured to direct the modulated optical wave at a mammal whose sentinel lymph nodes are to be imaged;
wherein the detector of each source-detector pair comprises an array of photo-sensitive detectors configured to detect fluorescent light emitted from a fluorescing material injected into said mammal whose sentinel lymph nodes are to be imaged;
an optical splitter coupled to the delivery optics to direct the modulated optical wave to a second photo-sensitive detector;
digital detector electronics coupled to said photo-sensitive detector array and to said second photo-sensitive detector configured to sample a first detector output from said photo-sensitive detector array and a second detector output from said second photo-sensitive detector, and further configured to perform a correlation of said detector array output with said second detector output for each source-detector pair to generate a temporal transfer correlation signal reflecting photon time-of-flight characteristics; and
an image reconstruction engine coupled to said digital detector electronics configured to reconstruct an image of an underlying tissue volume and sentinel lymph nodes based in part on the temporal transfer correlation signal.

10. The node imaging system of claim 9 wherein said first selected Golay code sequence has multiple repeats of the same pattern.

11. The node imaging system of claim 9 wherein said digital detector electronics is configured to utilize temporal over-sampling.

12. The node imaging system of claim 9 wherein said image reconstruction engine is configured to use an inversion technique.

13. The node imaging system of claim 12 wherein said inversion technique is singular-value decomposition.

14. The node imaging system of claim 12 wherein said inversion technique is Algebraic Reconstruction Technique.

* * * * *